(12) United States Patent
Badillo et al.

(10) Patent No.: US 11,463,828 B2
(45) Date of Patent: Oct. 4, 2022

(54) ACOUSTIC DEVICES WITH INWARDLY-FACING TRANSDUCERS

(71) Applicant: Knowles Electronics, LLC, Itasca, IL (US)

(72) Inventors: Dean Badillo, Schaumburg, IL (US); Matthew Manley, Crystal Lake, IL (US)

(73) Assignee: KNOWLES ELECTRONICS, LLC, Itasca, IL (US)

( * ) Notice: Subject to any disclaimer, the term of this patent is extended or adjusted under 35 U.S.C. 154(b) by 0 days.

(21) Appl. No.: 17/134,287

(22) Filed: Dec. 26, 2020

(65) Prior Publication Data
US 2021/0204079 A1    Jul. 1, 2021

Related U.S. Application Data

(60) Provisional application No. 62/954,295, filed on Dec. 27, 2019.

(51) Int. Cl.
| | |
|---|---|
| *H04R 25/00* | (2006.01) |
| *H04R 19/04* | (2006.01) |
| *A61B 8/02* | (2006.01) |
| *A61B 8/04* | (2006.01) |

(52) U.S. Cl.
CPC ............ *H04R 25/604* (2013.01); *A61B 8/02* (2013.01); *A61B 8/04* (2013.01); *H04R 19/04* (2013.01); *H04R 25/505* (2013.01); *H04R 25/609* (2019.05); *H04R 2201/003* (2013.01); *H04R 2225/021* (2013.01); *H04R 2225/025* (2013.01)

(58) Field of Classification Search
CPC .... H04R 25/604; H04R 19/04; H04R 25/505; H04R 2201/021; H04R 2201/025; H04R 2201/023; H04R 1/1075; H04R 1/1016
See application file for complete search history.

(56) References Cited

U.S. PATENT DOCUMENTS

| | | | |
|---|---|---|---|
| 6,654,468 B1 | 11/2003 | Thompson | |
| 7,065,220 B2 | 6/2006 | Warren et al. | |
| 7,471,798 B2 | 12/2008 | Warren | |
| 2002/0031234 A1 | 3/2002 | Wenger et al. | |
| 2005/0276433 A1* | 12/2005 | Miller | H04R 11/00 381/396 |
| 2011/0085675 A1 | 4/2011 | Wickstrom | |
| 2017/0214994 A1 | 7/2017 | Gadonniex et al. | |
| 2019/0208301 A1* | 7/2019 | Monti | H04R 1/1075 |
| 2019/0215620 A1* | 7/2019 | Albahri | H04R 25/554 |

OTHER PUBLICATIONS

Ytango; BTE with microphone and receiver in the canal-the world's first; dispenser sheet; 2013.

* cited by examiner

*Primary Examiner* — Sunita Joshi

(57) ABSTRACT

Sound-producing acoustic receivers and hearing devices implementing such receivers are disclosed. The acoustic receiver includes a receiver housing, an output port, a receiver motor assembly, and a transducer. The receiver housing includes a diaphragm that separates the receiver housing into a back volume and a front volume. The output port is located on the receiver housing and acoustically coupled to the front volume of the receiver housing. The receiver motor assembly is disposed in the back volume and is mechanically coupled to the diaphragm. The transducer is fastened to the receiver housing.

21 Claims, 9 Drawing Sheets

ACOUSTIC DEVICES WITH INWARDLY-FACING TRANSDUCERS

RELATED APPLICATIONS

This application claims priority to U.S. Provisional Patent Application Ser. No. 62/954,295 filed on Dec. 27, 2019, entitled "Acoustic Devices With Inwardly-Facing Transducers," the entire contents of which are hereby incorporated by reference.

TECHNICAL FIELD

This disclosure relates generally to acoustic devices and more specifically to acoustic devices with transducers fastened thereto.

BACKGROUND

Sound-producing acoustic devices including balanced armature receivers that convert an electrical input signal to an acoustic output signal characterized by a varying sound pressure level (SPL) are generally known. Such devices are used in hearing aids, headsets, hearables, ear buds among other hearing devices worn by a user. An acoustic receiver generally includes a motor and a coil to which an electrical excitation signal is applied. The coil is disposed about a portion of an armature (also known as a reed), a movable portion of which is disposed in equipoise between magnets, which are typically retained by a yoke. Application of the excitation or input signal to the receiver coil modulates the magnetic field, causing deflection of the reed between the magnets. The deflecting reed is linked to a movable portion (known as a paddle) of a diaphragm disposed within a partially enclosed receiver housing, wherein movement of the paddle forces air through a sound outlet or port of the housing. Additionally, some such hearing devices of the type described may be implemented with an outwardly facing microphone that detects ambient sound external to the ear canal, as generally known and used for noise-cancellation.

BRIEF DESCRIPTION OF THE DRAWINGS

The objects, features, and advantages of the present disclosure will be more apparent to those of ordinary skill in the art upon consideration of the following Detailed Description with reference to the accompanying drawings.

Figure 1:
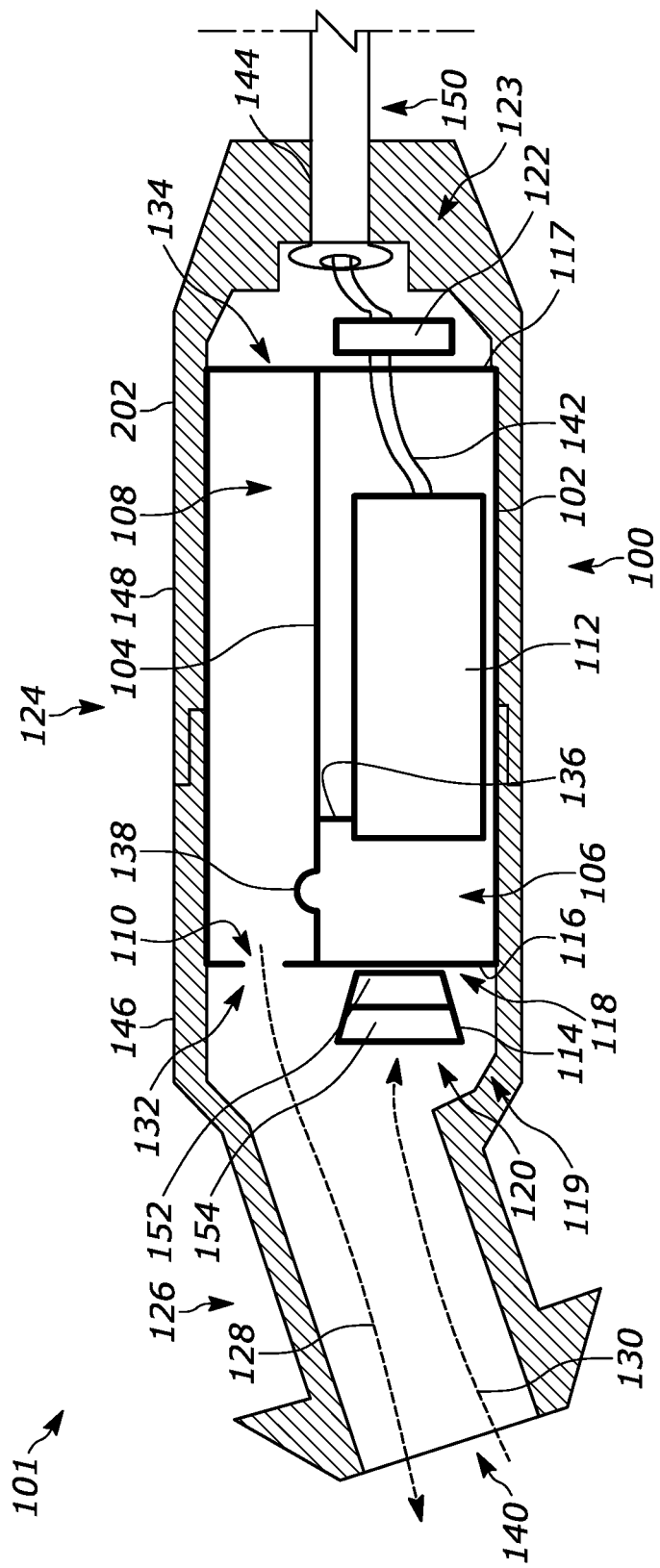
FIG. 1 is a diagram of a hearing device according to an embodiment.
Figure 2:
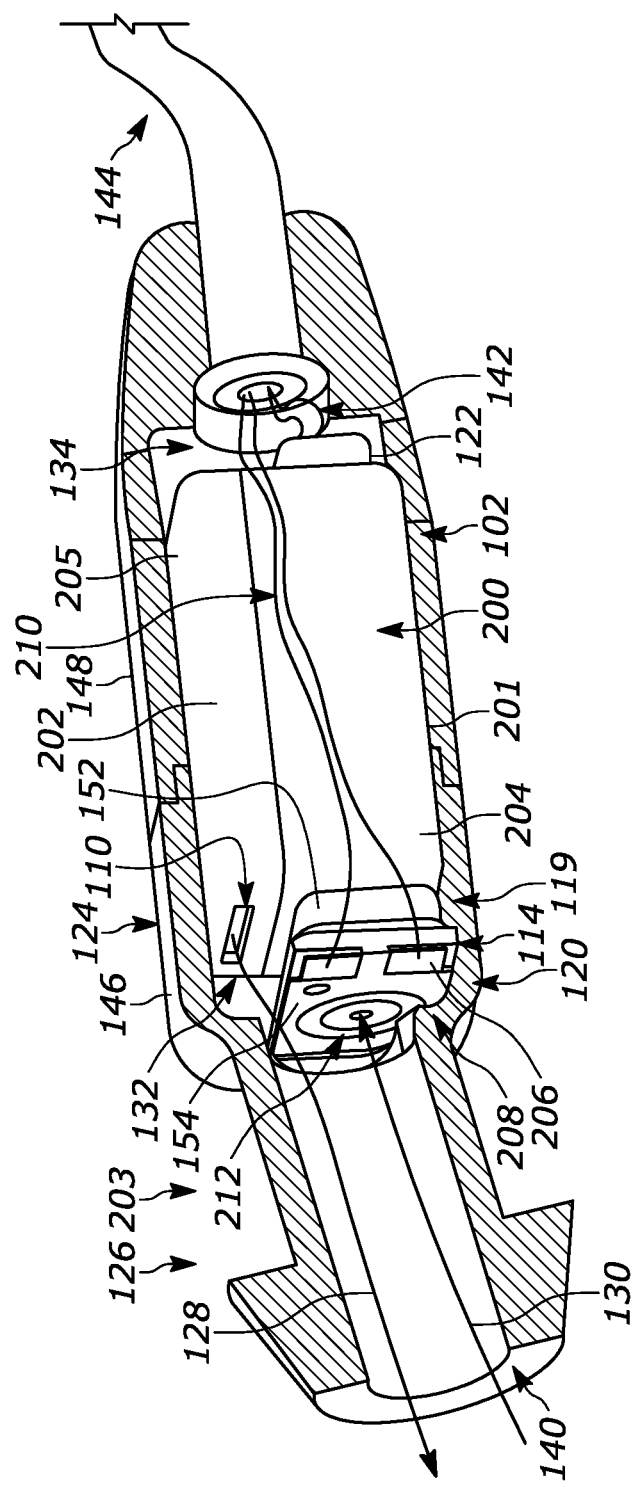
FIG. 2 is a cutaway view of the hearing device according to an embodiment.

Those of ordinary skill in the art will appreciate that elements in the figures are illustrated for simplicity and clarity. It will be further appreciated that certain actions or steps may be described or depicted in a particular order of occurrence while those of ordinary skill in the art will understand that such specificity with respect to sequence is not actually required unless a particular order is specifically indicated. It will also be understood that the terms and expressions used herein have the ordinary meaning as is accorded to such terms and expressions with respect to their corresponding respective fields of inquiry and study except where specific meanings have otherwise been set forth herein.

DETAILED DESCRIPTION

The present disclosure pertains to sound-producing acoustic receivers (also referred to herein as "receivers"). The receiver may be used in a receiver-in-canal (RIC) portion of a behind-the-ear (BTE) hearing device, an in-the-canal (ITC) or partially in-the-ear (ITE) hearing device, a wired or wireless earbud or earpiece, or as some other hearing device that produces an acoustic output signal in response to an electrical input signal and is intended for use on, in, or in close proximity to a user's ear.

The present disclosure pertains to sound-producing acoustic receivers that detect signals propagating from within the inner ear of a user. In certain implementations, sound-producing acoustic receivers are fitted with one or more inwardly-facing transducers. In some examples, an acoustic receiver includes a receiver housing that has a diaphragm separating the receiver housing into a back volume and a front volume. The acoustic receiver also includes an output port located on the receiver housing and acoustically coupled to the front volume of the receiver housing. The acoustic receiver also includes a receiver motor assembly disposed in the back volume such that the receiver motor assembly mechanically couples to the diaphragm. Furthermore, the acoustic receiver includes a transducer fastened to the receiver housing.

In some embodiments, the transducer is a microphone such as a microelectromechanical systems (MEMS) transducer or an electret condenser, for example. The transducer is fastened to the receiver housing in one of numerous different implementations. In some implementations, the transducer is fastened or attached to the receiver housing via any suitable method such as hooking, clamping, clipping, gluing, welding, taping, and soldering, among others. In some implementations, the transducer is fastened to the receiver housing such that the output port and the transducer are located on a common side of the receiver housing. In some implementations, the transducer is fastened to an end wall of the receiver housing that has the output port. In some implementations, the transducer is fastened so as to not obstruct the output port of the receiver housing. In some implementations, the transducer is fastened to an inner ear end of the receiver housing. In some implementations, the transducer is fastened to the receiver housing such that the transducer is oriented to detect signals propagating into the receiver housing via the sound opening.

In embodiments where the transducer is configured as a microphone assembly, the transducer comprises a housing including a sound port and a MEMS acoustic transducer disposed in the housing and acoustically coupled to the sound port. In one implementation, the housing of the microphone assembly is fastened to the receiver housing such that the sound port of the microphone assembly and the output port of the receiver housing are directed away from a common side of the receiver housing.

In some embodiments, the receiver housing has four side walls and two end walls such that a surface area of one of the side walls is greater than a surface area of one of the end walls, and the output port of the receiver housing is disposed in one of the end walls, with the transducer being fastened to the end wall that has the output port.

In one of these embodiments, the housing of the microphone assembly comprises a cover fastened to a base including the sound port and an electrical interface, such that the cover of the microphone assembly is fastened to the receiver housing. In another embodiment, a flex circuit is electrically coupled to contacts of the electrical interface of the microphone assembly. In yet another embodiment, the housing of the microphone assembly comprises a cover fastened to a base including an electrical interface. Also, the sound port is disposed in the cover, and the electrical interface of the microphone assembly is electrically coupled to an electrical interface disposed on the inner ear end of the receiver housing. In another embodiment, the electrical interface of the receiver housing has electrical contacts electrically coupled to electrical contacts of the electrical interface of the microphone assembly.

Alternatively, in another implementation, the housing of the microphone assembly is fastened to the receiver housing such that the sound port of the microphone assembly is directed toward the sound opening of the hearing device. In one embodiment of this implementation, the housing of the microphone assembly comprises a cover fastened to a base including the sound port and an electrical interface, such that the cover is fastened to the receiver housing. In another embodiment, the housing of the microphone assembly comprises a cover fastened to a base including an electrical interface, such that the sound port is disposed in the cover and the electrical interface of the microphone assembly is electrically coupled to an electrical interface disposed on the receiver housing.

The present disclosure also pertains to hearing devices that use the acoustic receivers as disclosed herein. For example, a hearing device includes the sound-producing acoustic receiver in an outer housing such that the receiver housing is at least partially disposed within the outer housing. The outer housing includes a sound-output nozzle disposed on a portion of the outer housing such that the nozzle is worn on or at least partially in a user's ear. Furthermore, the hearing device includes an electrical circuit operatively coupled to the acoustic receiver and to the transducer.

The electrical circuit is operable to determine one or more conditions according to one of numerous different implementations. In some implementations, the electrical circuit determines at least one biometric condition of the user based upon a signal from the transducer. Examples of such biometric condition include one or more of: heartrate, pulse rate, or blood pressure, among others. In some implementations, the electrical circuit determines an acoustic leakage between the outer housing and a user's ear based upon the signal from the transducer. In some implementations, the electrical circuit determines a presence of an obstruction in an acoustic passage based upon the signal from the transducer. In some implementations, the electrical circuit filters out acoustic signals, emanating from the output port, from the acoustic signals detected by the transducer in order to obtain inner ear acoustic signals to improve biometric, leakage or obstruction detection.

Details regarding the receiver, the hearing device, and the electrical circuit will be disclosed below in further details, with embodiments provided as nonlimiting examples of the different configurations and embodiments provided herein.

FIGS. 1 through 7 show examples of a hearing device 101 that uses an acoustic receiver 100 as explained above, according to embodiments as disclosed herein. In some examples, the acoustic receiver 100 is any suitable armature-based receiver as known in the art. The acoustic receiver 100 includes a receiver housing 102 with diaphragm 104 between a back volume 106 and a front volume 108 as well as an output port 110 acoustically coupled to the front volume 108. A receiver motor assembly 112 is disposed in the back volume 106 and mechanically coupled to the diaphragm 104. A transducer 114 is fastened to the receiver housing 102.

The receiver motor assembly 112 of the armature-based receiver 100 includes a link 136 that movably couples with the diaphragm 104 at a hinge 138 such that actuation of the receiver motor assembly 112 causes movement of the diaphragm 104 to create acoustic signals within the front volume 108. The acoustic signals are then propagated from the front volume 108 through the output port 110 and into the ear canal along a direction of the output acoustic passage 128. The receiver motor assembly 112 is controlled via wires 142 extending therefrom and leading to an electrical terminal or interface 122 of the receiver 100. The electrical interface 122 attaches to the receiver housing 102 at the outer ear end 134, after which the wires 142 lead into a cable 144 coupled to a BTE unit. In other applications, the receiver is electrically coupled to electrical components housed within the outer housing as in the case of an ear worn hearing device. Such devices include ITE and ITC hear aids, True Wireless Stereo (TWS) devices, among other hearing devices.

The receiver housing 102 has an end wall 116 with an outer surface 118 onto which the transducer 114 can be fastened in some embodiments, such those shown in FIGS. 1 through 4. In some embodiments, the outer surface 118 has a recessed portion or a coupling member to assist in fastening the transducer 114 thereto. The receiver housing 102 has another end wall 117 into which the electrical interface 122 can be fastened or attached. The two opposing end walls 116 and 117 correspond to the walls of the receiver housing 102 that define the inner ear end 132 and the outer ear end 134, respectively. The receiver housing 102 has additional walls on the side, named side walls. In the example shown, the receiver housing 102 assumes a shape that generally resembles a rectangular prism that has six sides. In such an example, the receiver housing 102 has four side walls 200, 201, 203, and 205 in addition to the two end walls 116 and 117.

In some examples, a surface area of one of the side walls 200, 201, 203, and 205 is greater than a surface area of one of the end walls 116 and 117. The output port 110 of the receiver housing 102 is disposed in one of the end walls 116 and 117, and the transducer 114 is fastened to the end wall 116 or 117 that has the output port 110. The end wall 116 includes both the output port 110 and the transducer 114 fastened thereto.

In some examples, the transducer 114 is a MEMS acoustic transducer in a microphone assembly 119. The microphone assembly 119 has a housing 120 with a sound port 212. The housing 120 is formed by fastening two separate components: a cover 152 and a base 154. The transducer 114 is disposed in the housing 120 and acoustically coupled to the sound port 140. The base 154 includes the sound port 212 and an electrical interface 208, and the cover 154 of the microphone assembly 119 is fastened to the receiver housing 102, such that the sound port 212 of the microphone assembly 119 and the output port 110 of the receiver housing 102 are directed away from the end wall 116. In some examples, the sound port 212 of the microphone assembly 119 is directed toward the sound opening 140 of the hearing device 101.

Furthermore, the electrical interface 208 of the microphone assembly 119 has electrical contacts 206 with wires 210 leading therefrom. Examples of electrical contacts include pins, friction contacts, and solder pads, although other suitably configured structures can also be used. In the example shown, the wires 210 are directed around the receiver housing 102 toward the outer ear end 134, after which the wires 210 are led into the same cable 144 that also contains the wires 142 leading from the receiver 100, as previously explained. As such, the wires 210 enables electrical signals to be transmitted between the microphone assembly 119 and an external electrical circuit.

In some examples, the receiver housing 102 is formed by fastening two separate components together: a cover 202 and a base 204. The cover 202 defines the front volume 108 as well as the output port 110, and the base 204 defines the back volume 106. Similarly, the outer housing 124 is also formed by fastening two separate components together: an inner ear component 146 and an outer ear component 148. The inner ear component 146 defines the output nozzle 126, and the outer ear component 148 defines an aperture 150 in the outer housing 124 through which the cable 144 passes to receive the wires 142 and 210.

In some examples, the output nozzle 126 is directed at an offset angle with respect to a longitudinal axis formed by the length of the receiver housing 102. For example, the output nozzle 126 may be directed at an angle of between 10 and 20 degrees, 20 and 30 degrees, 30 to 40 degrees, 40 to 50 degrees, 50 to 60 degrees, 60 to 70 degrees, or greater than 70 degrees with respect to the longitudinal axis of the receiver housing 102, as appropriate.

Figure 3:
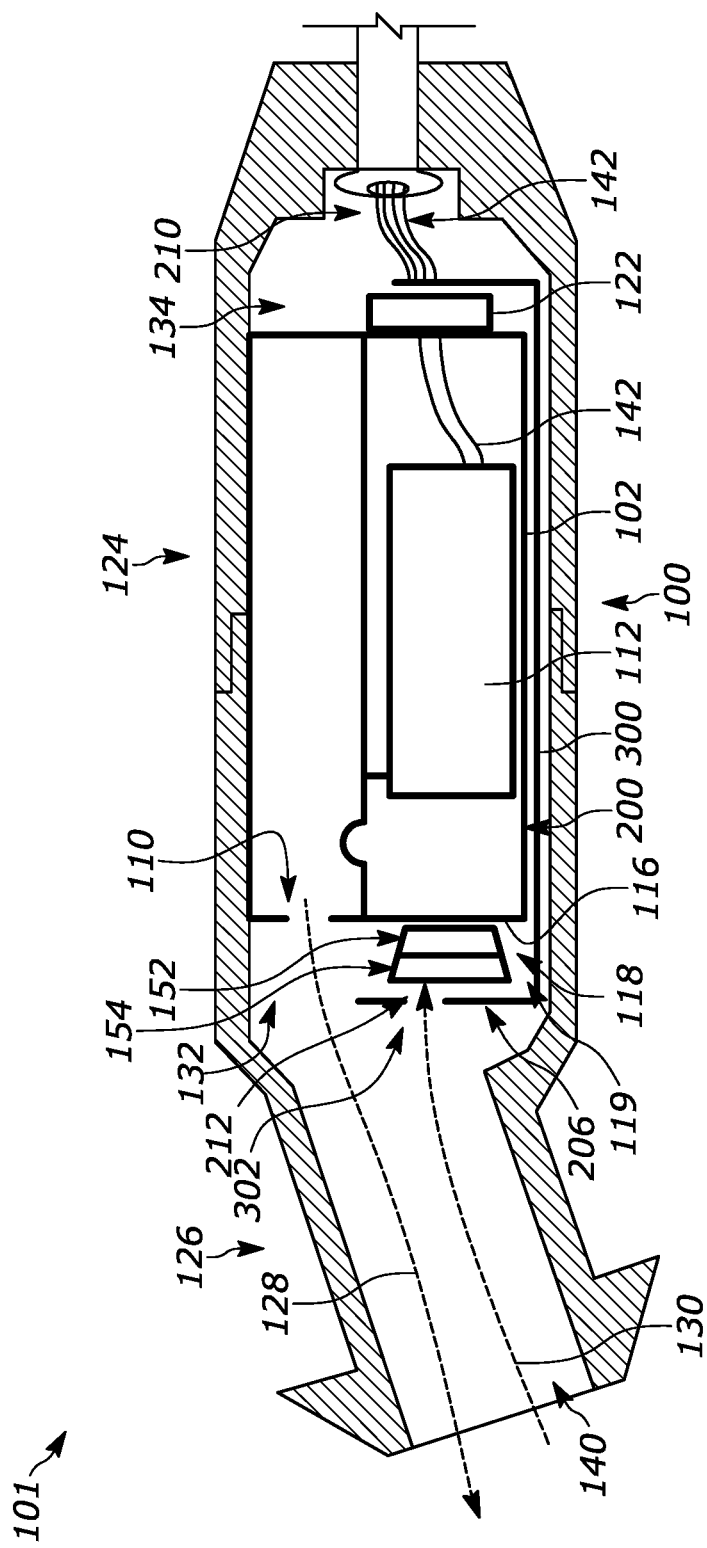
FIG. 3 is a diagram of a hearing device according to an embodiment.
Figure 4:
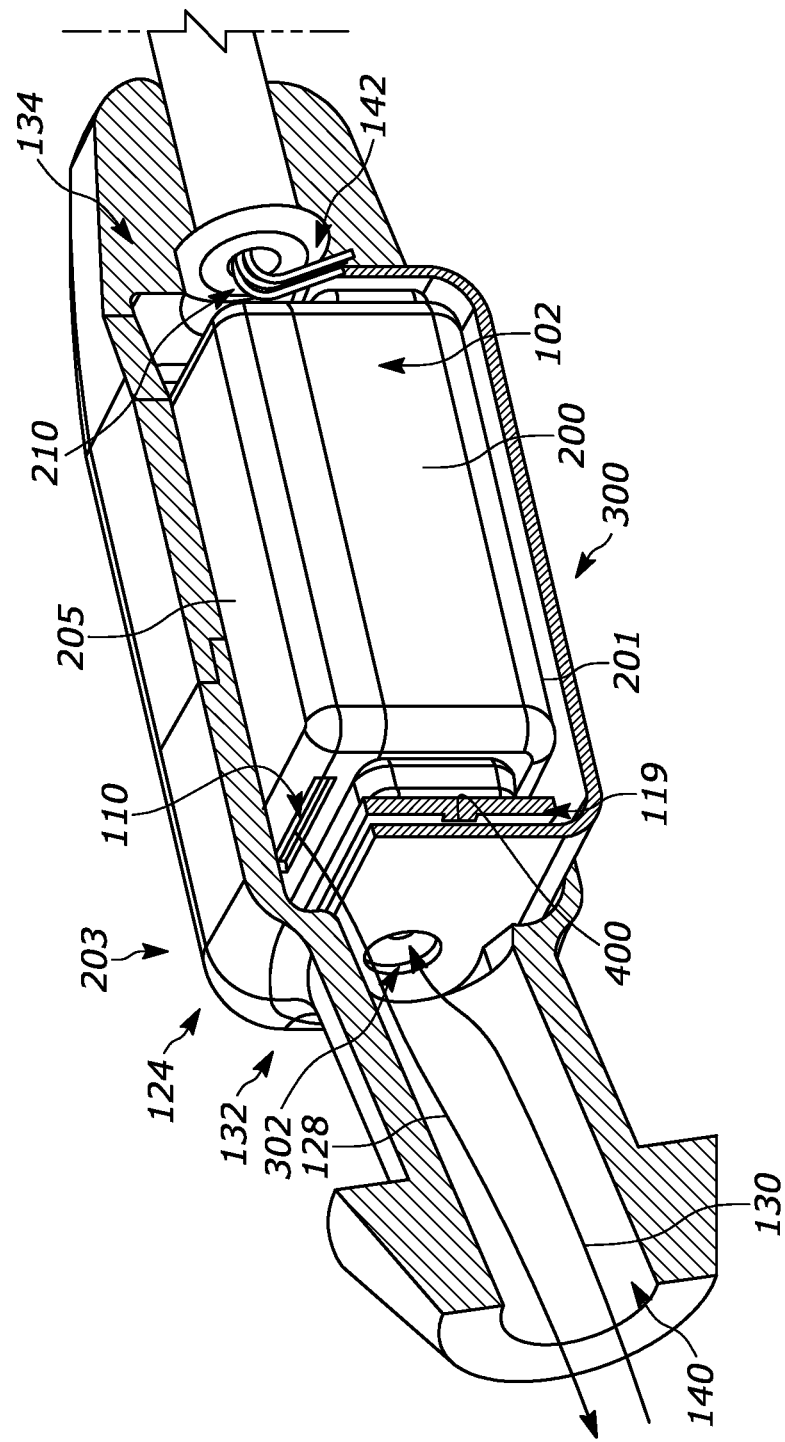
FIG. 4 is a cutaway view of a hearing device according to an embodiment.

In FIGS. 3 and 4, a flex circuit 300 is electrically coupled to the contacts 206 of the electrical interface 208 of the microphone assembly 119. The flex circuit 300 is disposed external to the receiver housing 102 and internal to the outer housing 124. Furthermore, the flex circuit 300 is formed as a cup or base member such that only a bottom side wall 201 is fixedly attached or fastened to the flex circuit 300 in some examples. In some examples, more than one of the side walls 200, 201, and 203 (i.e., any of the side walls except for a top side wall 205) can be fixedly attached to the flex circuit 300. In some examples, the microphone assembly 119, or the housing 120 thereof, is fixedly attached or fastened to an internal surface 400 of the flex circuit 300.

Instead of the wires 210 extending from the electrical interface 208 of the microphone assembly 119 as done in FIG. 1, the flex circuit 300 extends the length of the receiver housing 102. The flex circuit 300 has flexible circuit portions printed thereon, for example via photolithographic technology to form copper strips extending from one end of the flex circuit 300 to the other end, although any other suitable techniques and conductive materials may be employed.

The flex circuit 300 enables the electrical interface 208 to be electrically coupled with the external electrical circuit (not shown). Specifically, the flex circuit 300 electrically couples the electrical interface 208 of the microphone assembly 119 to the electrical interface 122 of the receiver housing 102. By doing so, the electrical contacts 123 of the electrical interface 122 of the receiver housing 102 are electrically coupled to the electrical contacts 206 of the electrical interface 208 of the microphone assembly 119.

The set of wires 142 that extend from the receiver motor assembly 112 are attached to one surface of the flex circuit 300, whereas two set of wires 142 and 210 extend from the other surface of the flex circuit 300. The wires 142 transmit electrical signals between the receiver motor assembly 112 and the external electrical circuit, and the wires 210 transmit electrical signals between the transducer 114 (or the microphone assembly 119) and the external electrical circuit.

Furthermore, the cover 152 is fastened to the receiver housing 102 (or more specifically, to the outer surface 118 of the end wall 116 that defines the inner ear end 132) and the base 154 is fastened to the flex circuit 300. The flex circuit 300 includes an aperture 302 for the sound port 212 disposed in the cover 152 to acoustically couple the transducer 114 or the microphone assembly 119 with the sound port 140.

Figure 5:
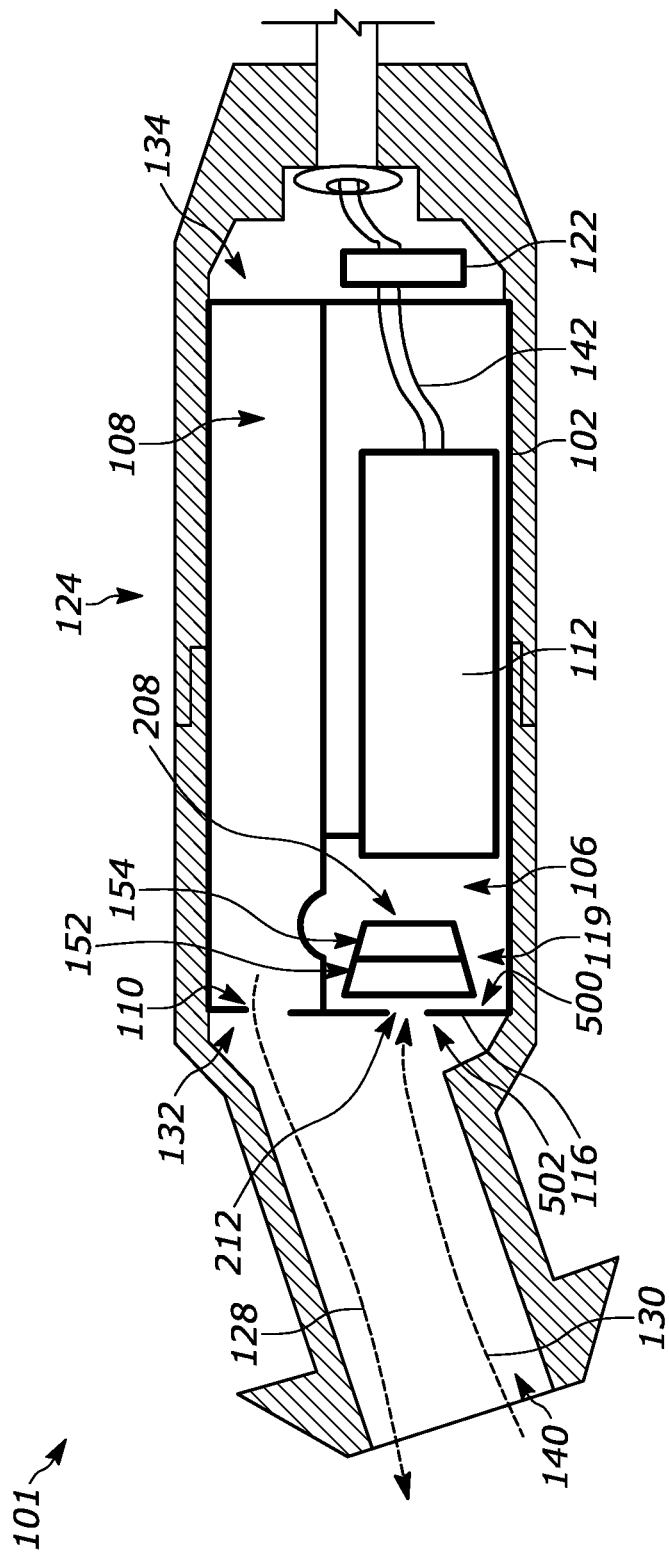
FIG. 5 is a diagram of a hearing device according to an embodiment.
Figure 6:
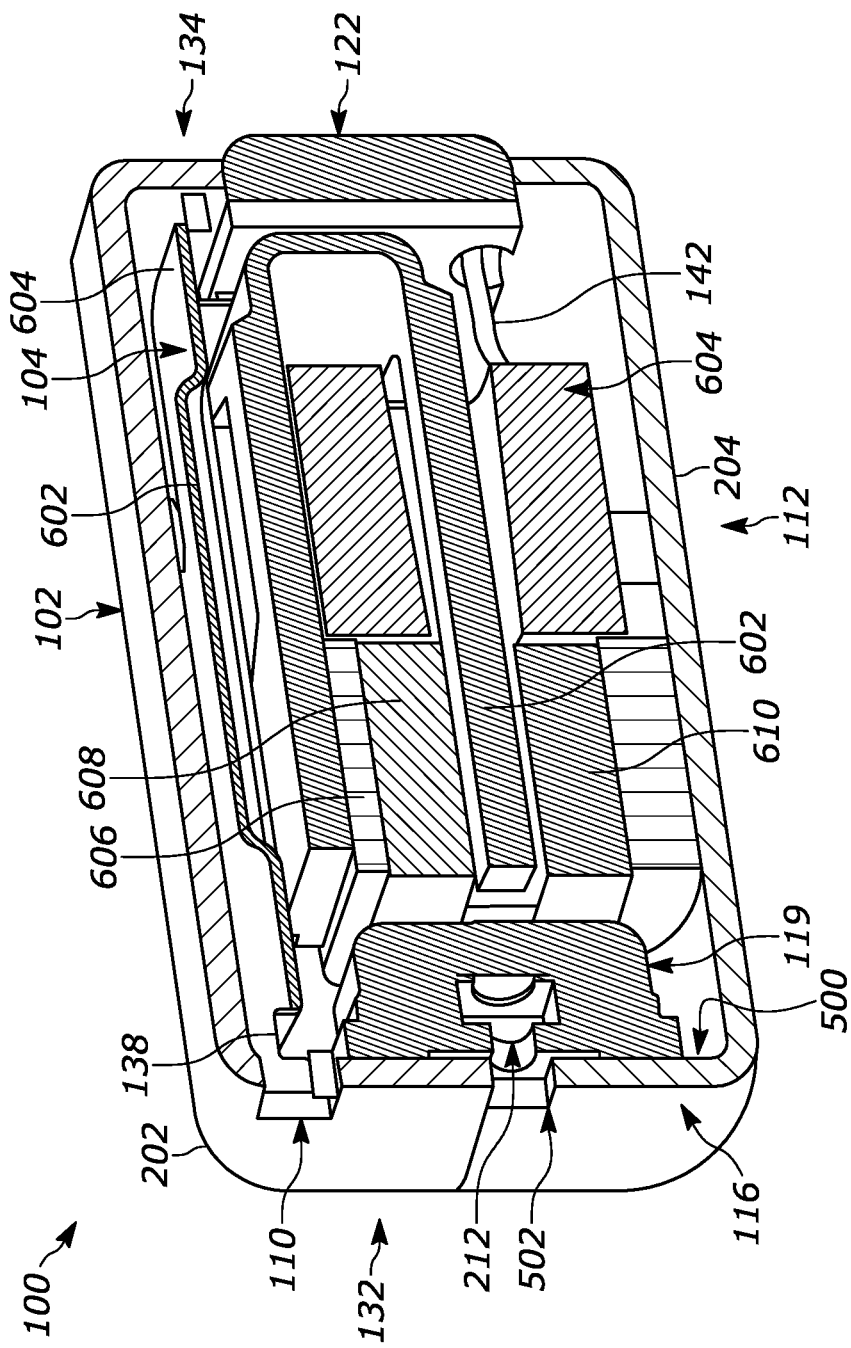
FIG. 6 is a cutaway view of an acoustic receiver as used in a hearing device according to an embodiment.

In FIGS. 5 and 6, the microphone assembly 119 (or the transducer 114) is fixedly attached or fastened to an inner surface 500 of the end wall 116 that defines the inner ear end 132, instead of to the outer surface 118. The receiver housing 102 has two separate and distinct ports for the output acoustic passage 128 and the input acoustic passage 130. Specifically, the cover 202 defines the output port 110 from which the output acoustic passage 128 extends, and the base 204 defines an input port 502 that acoustically couples the sound port 212 of the microphone assembly 119 and the sound opening 140 of the outer housing 124, which defines the input acoustic passage 130.

In some examples, the microphone assembly 119 has the cover 120 formed by fastening the cover 152 with the base 154. The cover 152 defines the portion that attaches or fastens to the inner surface 500 of the end wall 116, and also defines the sound port 212 of the microphone assembly 119. Furthermore, the base 154 includes the electrical interface 208 that is electrically coupled to the electrical interface 122 via wires (not shown) that extend from the base 154 toward the electrical interface 122. In some examples, the wires extend within the receiver housing 102 in the back volume 106, while in other examples, the wires extend between the receiver housing 102 and the outer housing 124.

FIG. 6 shows the individual components of the receiver motor assembly 112 used in the acoustic receiver 100 according to some embodiments. For example, the receiver motor assembly 112 includes a paddle 600, an armature 602 (also known as a reed), and one or more coil 604. The paddle 600, which is a part of the diaphragm 104, is supported on one end by a support structure 604 moveably coupling the paddle 600 to the receiver housing 102 at the hinge 138. The receiver housing 102 additionally includes a yoke 606 which holds a pair of magnets 608 and 610 between which a portion of the armature 602 movably extends. The link 136 (not shown in FIG. 6) connects the armature 602 with the paddle 600 such that the armature 602 deflects relative to the magnets 608 and 610 in response to application of an electrical signal to the coil 604.

Figure 7:
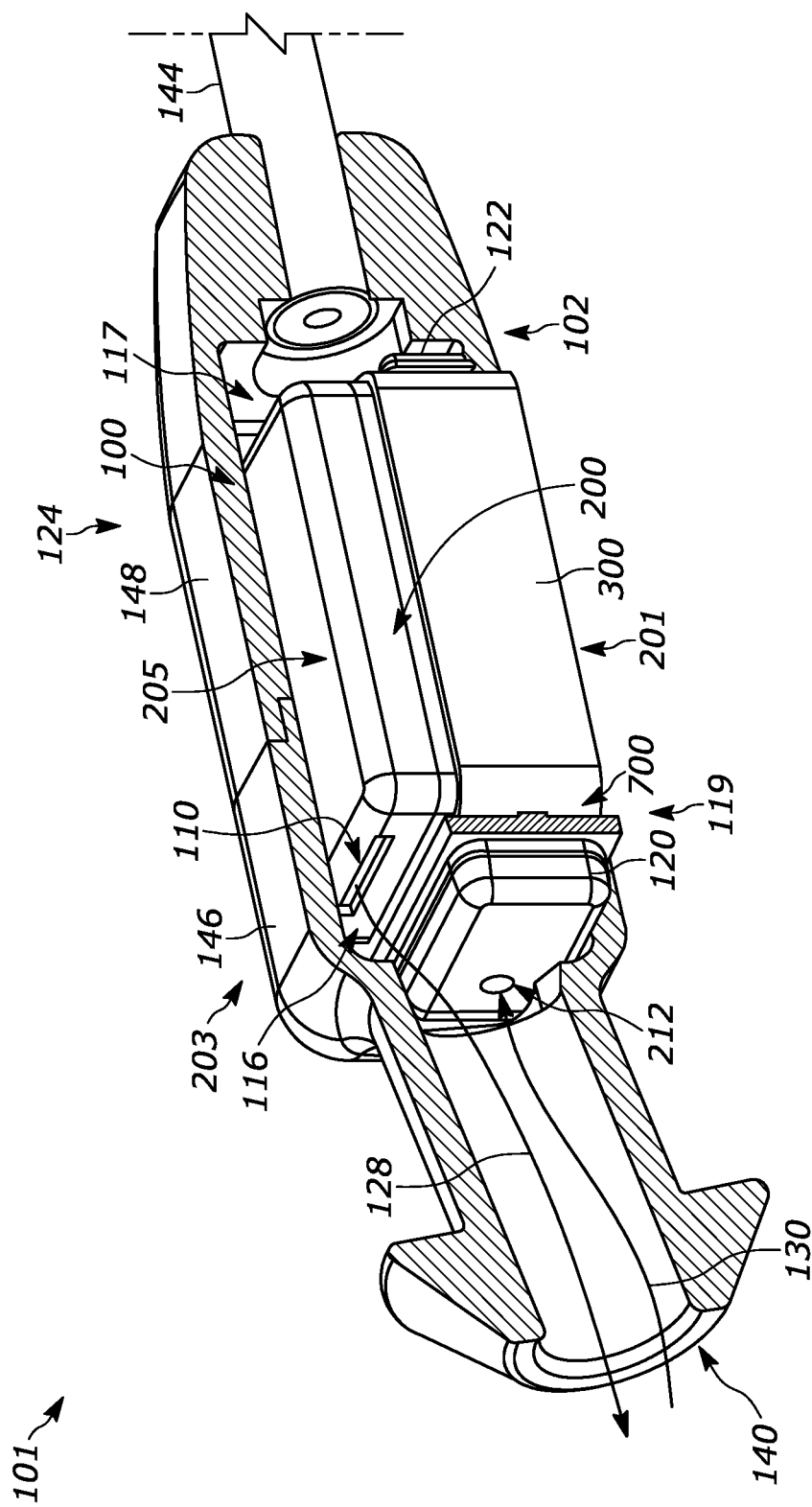
FIG. 7 is a cutaway view of a hearing device according to an embodiment.

In FIG. 7, the flex circuit 300 is electrically coupled to the microphone assembly 119 such that the flex circuit 300 is fixedly attached or fastened to the end walls 116 and 117 as well as at least one side wall. The flex circuit 300 is positioned between the microphone assembly 119 and the receiver housing 102. The microphone assembly 119, or in some examples the housing 120 of the microphone assembly 119, is fixedly attached or fastened to an external surface 700 of the flex circuit 300. In some examples, the flex circuit 300 is fixedly attached or fastened to one or more of the side walls; for example, more than one of the side walls 200, 201, and 203 (i.e., any of the side walls except for a top side wall 205) can be fixedly attached to the flex circuit 300. In some examples, the electrical interface (not shown) of the microphone assembly 119 is electrically coupled to the electrical interface 122 disposed on either the receiver housing 102 or the flex circuit 300. For simplicity, the wires 142 for the receiver 100 and the wires 210 for the microphone assembly 119 are not shown in FIG. 7.

Instead of the wires 210 extending from the electrical interface 208 of the microphone assembly 119 as done in FIG. 1, the flex circuit 300 extends the length of the receiver housing 102. The flex circuit 300 has flexible circuit portions printed thereon, for example via photolithographic technology to form copper strips extending from one end of the flex circuit 300 to the other end, although any other suitable techniques and conductive materials may be employed.

The flex circuit 300 enables the electrical interface 208 to be electrically coupled with the external electrical circuit (not shown). Specifically, the flex circuit 300 electrically couples the electrical interface 208 of the microphone assembly 119 to the electrical interface 122 of the receiver housing 102. By doing so, the electrical contacts 123 of the electrical interface 122 of the receiver housing 102 are electrically coupled to the electrical contacts 206 of the electrical interface 208 of the microphone assembly 119.

The set of wires 142 that extend from the receiver motor assembly 112 are attached to one surface of the flex circuit 300, whereas two set of wires 142 and 210 extend from the other surface of the flex circuit 300. The wires 142 transmit electrical signals between the receiver motor assembly 112 and the external electrical circuit, and the wires 210 transmit electrical signals between the transducer 114 (or the microphone assembly 119) and the external electrical circuit.

Figure 8:
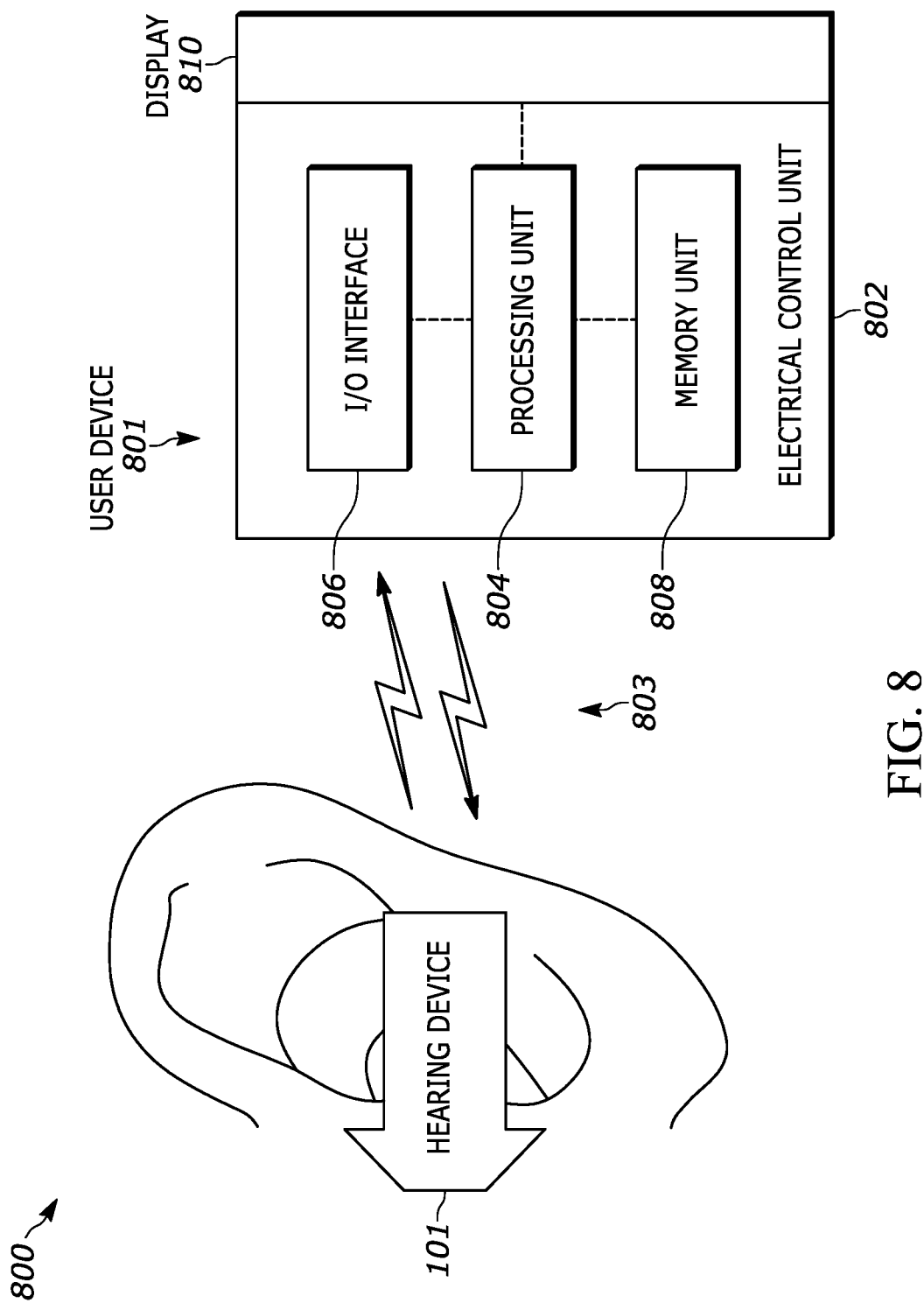
FIG. 8 is a schematic diagram of a hearing device system according to an embodiment.

FIG. 8 shows an example of a system 800 which incorporates the hearing device 101 as explained above, according to some embodiments as disclosed herein. The system 800 includes a user device 801, for example a smartphone, personal computer, smart watch, wearable or other device that communicates with the hearing device 101 via an electrical connection 803. The electrical connection 803 may be wired or wireless, using any suitable data transmission technology known in the art, including but not limited to Bluetooth and infrared transmission, for example. The user device 801 includes a processing unit 804 (also referred to herein as an electrical circuit), an input/output (I/O) interface 806, and a memory unit 808. In some examples, the user device 810 also includes a display 810. In some examples, the I/O interface may be wired or wireless to form the electrical connection 803 with the hearing device 101. The memory unit 808 may be any suitable memory including but not limited to a register, random-access memory, read-only memory, or flash memory. The processing unit 804 may be any suitable processor including but not limited to a central processing unit (CPU) or a system-on-a-chip (SoC). The I/O interface 806 receives data transmitted from the hearing device 101 to be analyzed by the processing unit 804, and also transmits data from the processing unit 804 to the hearing device 101. The display 810 shows notifications sent from the processing unit 804 in the event that the processing unit 804 detects a predetermined condition, as explained below.

Figure 9:
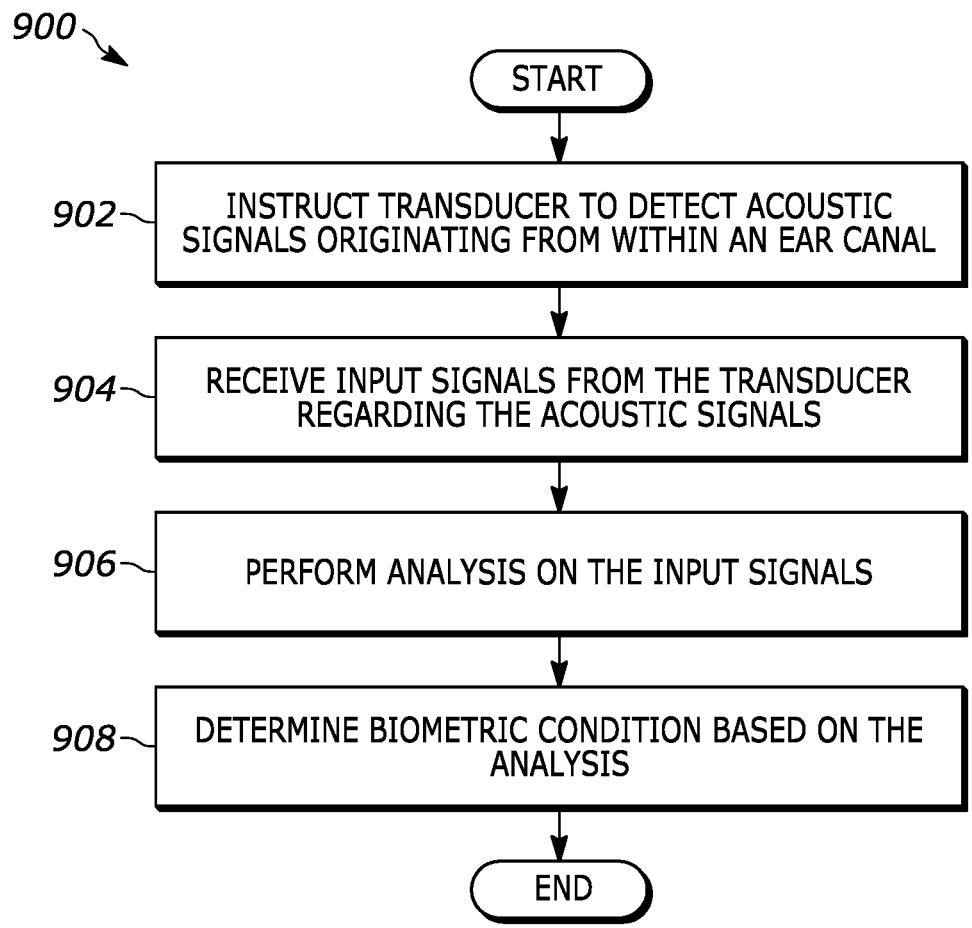
FIG. 9 is a flow diagram of a method according to an embodiment.

FIG. 9 shows a method 900 for detecting a predetermined condition using the acoustic receiver 100 according to some embodiments. In step 902, the transducer 114 of the receiver 100 is instructed to detect acoustic signals originating from within an ear canal, or inner ear, with which the transducer 114 is acoustically coupled. In step 904, the processing unit 804 receives input signals from the transducer 114 regarding the acoustic signals that are detected. In step 906, the processing unit 804 performs an analysis on the input signals based upon instructions (e.g., processing algorithm) that are stored in the memory unit 808 coupled with the processing unit 804. In step 908, the processing unit 804 determines one or more biometric conditions based upon the performed analysis. The biometric conditions include one or more of: heartrate, pulse rate, or blood pressure of the user.

In some examples, instead of or in addition to the biometric condition(s), the processing unit 804 also determines other conditions, such as an acoustic leakage between the outer housing 124 and the user's ear canal, based upon the input signal transmitted from the transducer 114. In some examples, the other conditions include the presence of any obstruction in an acoustic passage (e.g., 128 and/or 130), which the processing unit 804 determines based upon the input signal transmitted from the transducer 114. In some examples, the acoustic leakage and the obstruction (for example, wax buildup) are detected by solely analyzing the input acoustic signals detected by the transducer 114. In some examples, such conditions are detected by analyzing a difference between the acoustic signals emanating from the output port 110 and the input acoustic signals that are reflected back from the inner ear and detected by the transducer 114.

Specifically, the difference between the input and output signals may indicate the extent to which the condition of the acoustic device has changed relative to the particular state or reference condition. For example, where the change in condition results from an obstruction due to wax accumulation in the acoustic device, the extent of the difference may indicate the extent of the obstruction. In this example, the processing algorithm could be configured to provide an alert when the obstruction exceeds a threshold and/or store such information for interrogation by the user or a technician. Such algorithms may be configured similarly for detecting changes in other conditions or states, examples of which are described herein.

In some examples, prior to performing analysis on the input signal from the transducer 114, the processing unit 804 temporarily halts or reduces the acoustic signals propagating from the output port 110 of the receiver 100, in order to reduce the noises that may be present in the atmosphere that is acoustically coupled with the sound port 212 of the transducer 114. In some examples, the analysis is performed upon detection of a reduction in the acoustic signals from the output port 110, such as when the acoustic receiver 100 is not receiving any input or when the acoustic receiver 100 is between two tracks of songs that are being played.

In some examples, the processing unit 804 filters out acoustic signals that emanate from the output port 110, from the acoustic signals detected by the transducer 114, in order to obtain inner ear acoustic signals. In some examples, the processing unit 804 filters out a frequency range that is greater than 20 Hz, greater than 15 Hz, greater than 10 Hz, or greater than 5 Hz, as suitable. After the frequency range is filtered out, the remaining frequency range of the detected signal is analyzed by the processing unit 804.

Upon detecting the predetermined condition as explained above, the processing unit 804 sends a notification indicating the detected condition to be displayed on the display 810. In some examples, the notification is also sent by remote communication to a remote device which may be, for example, another user device such as a smartphone, wearable, or other mobile device, via the I/O interface 806, which includes a wireless transmitter. Additionally, or alternatively, the remote device is a cloud-based server, or a diagnostic test system which diagnoses the acoustic receiver. In one aspect of this embodiment, the remote device is a computer used by an audiologist to whom the hearing device transmits data such that the audiologist can keep track of the status of the hearing devices of his or her customers.

Alternatively, some or all of the processing of the signal from the transducer in the hearing device (e.g., for detection of biometric, leakage, obstruction, etc.) is performed by a processor integrated in the hearing device. Depending on the use case some or all of the processed transducer signal results may be communicated to the user device. For example, it may be desirable to transit biometric information to the user device for consumption (e.g., viewing) on the user device or for further processing. In other cases, the processed results may be used to provide or trigger a user alert (e.g., leakage or obstruction) by the hearing device without transmitting the results to a user device. The processed results may also be stored in memory on the hearing device for later interrogation by the user or a technician.

While the present disclosure and what is presently considered to be the best mode thereof has been described in a manner that establishes possession by the inventors and that enables those of ordinary skill in the art to make and use the same, it will be understood and appreciated that there are many equivalents to the exemplary embodiments disclosed herein and that myriad modifications and variations may be made thereto without departing from the scope and spirit of the disclosure, which is to be limited not by the exemplary embodiments but by the appended claims.

What is claimed is:

1. A sound-producing acoustic receiver comprising:
   a receiver housing having a diaphragm separating the receiver housing into a back volume and a front volume;
   an output port located on the receiver housing and acoustically coupled to the front volume of the receiver housing;
   a receiver motor assembly disposed in the back volume, the receiver motor assembly mechanically coupled to the diaphragm; and
   a transducer fastened to the receiver housing.

2. The receiver of claim 1, wherein the output port and the transducer are located on a common side of the receiver housing.

3. The receiver of claim 2, wherein the receiver housing comprises an end wall, and wherein the transducer is fastened to an outer surface of the end wall.

4. The receiver of claim 1, wherein the transducer is a microphone assembly comprising a housing including a sound port and a microelectromechanical systems (MEMS) acoustic transducer disposed in the housing and acoustically coupled to the sound port, the housing of the microphone assembly fastened to the receiver housing, wherein the sound port of the microphone assembly and the output port of the receiver housing are directed away from a common side of the receiver housing.

5. The receiver of claim 4, the receiver housing comprising four side walls and two end walls, a surface area of one of the side walls greater than a surface area of one of the end walls, the output port of the receiver housing disposed in one of the end walls and the transducer fastened to the end wall having the output port.

6. The receiver of claim 5, the housing of the microphone assembly comprising a cover fastened to a base including the sound port and an electrical interface, the cover of the microphone assembly fastened to the receiver housing.

7. The receiver of claim 6 further comprising a flex circuit electrically coupled to contacts of the electrical interface of the microphone assembly.

8. The receiver of claim 5, the housing of the microphone assembly comprising a cover fastened to a base including an electrical interface, the sound port disposed in the cover and the electrical interface of the microphone assembly electrically coupled to an electrical interface disposed on the end of the receiver housing.

9. The receiver of claim 8, the electrical interface of the receiver housing having electrical contacts electrically coupled to electrical contacts of the electrical interface of the microphone assembly.

10. The receiver of claim 5, wherein the transducer does not obstruct the output port of the receiver housing.

11. A hearing device comprising:
    a sound-producing acoustic receiver comprising:
       a receiver housing having a diaphragm separating the receiver housing into a back volume and a front volume, the receiver housing comprising an inner ear end and an outer ear end;
       an output port located in the receiver housing and acoustically coupled to the front volume of the receiver housing;
       a receiver motor assembly disposed in the back volume, the receiver motor assembly mechanically coupled to the diaphragm; and
       a transducer fastened to the inner ear end of the receiver housing;
    an outer housing in which the receiver housing is at least partially disposed, the outer housing comprising a sound-output nozzle disposed on a portion of the outer housing configured to be worn on or at least partially in a user's ear; and
    an electrical circuit operatively coupled to the acoustic receiver and to the transducer.

12. The hearing device of claim 11, wherein the electrical circuit is configured to determine at least one biometric condition of the user based on a signal from the transducer.

13. The hearing device of claim 12, wherein the at least one biometric condition includes one or more of: heartrate, pulse rate, or blood pressure.

14. The hearing device of claim 11, wherein the electrical circuit is configured to determine an acoustic leakage between the outer housing and a user's ear based on a signal from the transducer.

15. The hearing device of claim 14, wherein the electrical circuit is configured to determine presence of an obstruction in an acoustic passage based on a signal from the transducer.

16. The hearing device of claim 10, wherein the electrical circuit is configured to filter out acoustic signals, emanating from the output port, from the acoustic signals detected by the transducer to obtain inner ear acoustic signals.

17. A hearing device comprising:
    an outer housing having a sound opening on a portion of the outer housing configured to be worn on, or partially in, a user's ear;
    a sound-producing acoustic receiver disposed in the outer housing, the acoustic receiver comprising:
       a receiver housing having a diaphragm separating the receiver housing into a back volume and a front volume, the receiver housing comprising an inner ear end and an outer ear end;
       a sound port located in the receiver housing, the sound port acoustically coupling the front volume of the receiver housing to the sound opening;

a motor assembly disposed in the back volume, the motor assembly mechanically coupled to the diaphragm; and a transducer fastened to the receiver housing and orientated to detect signals propagating into the outer housing via the sound opening.

18. The hearing device of claim 17, the transducer is a microphone assembly including a housing having a sound port and a microelectromechanical systems (MEMS) acoustic transducer disposed in the housing, the housing of the microphone assembly fastened to the receiver housing and the sound port of the microphone assembly directed toward the sound opening of the hearing device.

19. The hearing device of claim 18, the housing of the microphone assembly comprising a cover fastened to a base including the sound port and an electrical interface, the cover fastened to the receiver housing.

20. The hearing device of claim 19 further comprising a flex circuit electrically coupled to contacts of the electrical interface of the microphone assembly.

21. The hearing device of claim 18, the housing of the microphone assembly comprising a cover fastened to a base including an electrical interface, the sound port disposed in the cover and the electrical interface of the microphone assembly electrically coupled to an electrical interface disposed on the receiver housing.

* * * * *